(12) United States Patent
Kojima et al.

(10) Patent No.: US 9,670,148 B2
(45) Date of Patent: Jun. 6, 2017

(54) METHOD FOR PRODUCING META-XYLYLENEDIISOCYANATES

(71) Applicant: MITSUI CHEMICALS, INC., Minato-ku, Tokyo (JP)

(72) Inventors: Kouya Kojima, Urayasu (JP); Hidetaka Tsukada, Omuta (JP); Mamoru Takashina, Tallahassee, FL (US); Chitoshi Shimakawa, Arao (JP); Naoyuki Kakinuma, Omuta (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/903,268

(22) PCT Filed: Aug. 11, 2014

(86) PCT No.: PCT/JP2014/071245
§ 371 (c)(1),
(2) Date: Jan. 6, 2016

(87) PCT Pub. No.: WO2015/025773
PCT Pub. Date: Feb. 26, 2015

(65) Prior Publication Data
US 2016/0145201 A1  May 26, 2016

(30) Foreign Application Priority Data

Aug. 23, 2013 (JP) ................. 2013-173457

(51) Int. Cl.
| | |
|---|---|
| C07C 263/06 | (2006.01) |
| C07C 263/04 | (2006.01) |
| C07C 269/00 | (2006.01) |
| C07C 273/18 | (2006.01) |
| C07C 271/20 | (2006.01) |
| C07C 209/48 | (2006.01) |
| C07C 253/28 | (2006.01) |

(52) U.S. Cl.
CPC .......... *C07C 263/06* (2013.01); *C07C 263/04* (2013.01); *C07C 269/00* (2013.01); *C07C 273/1809* (2013.01); *C07C 209/48* (2013.01); *C07C 253/28* (2013.01); *C07C 271/20* (2013.01)

(58) Field of Classification Search
CPC ... C07C 263/00; C07C 263/04; C07C 263/06; C07C 273/2809; C07C 209/48; C07C 271/20; C07C 253/28; C07C 273/1809
See application file for complete search history.

(56) References Cited

U.S. PATENT DOCUMENTS

| | | | | |
|---|---|---|---|---|
| 4,415,745 A | * | 11/1983 | Ryu ...................... | C07C 263/04 558/411 |
| 5,196,572 A | * | 3/1993 | Okawa ................ | C07C 263/04 521/159 |
| 5,502,244 A | | 3/1996 | Okawa et al. | |
| 2002/0038054 A1 | | 3/2002 | Nakamura et al. | |
| 2012/0271067 A1 | | 10/2012 | Shimokawatoko et al. | |
| 2013/0023691 A1 | | 1/2013 | Okazoe et al. | |

FOREIGN PATENT DOCUMENTS

| | | |
|---|---|---|
| CN | 102652124 A | 8/2012 |
| EP | 0492145 A2 | 7/1992 |
| EP | 2554537 A1 | 2/2013 |
| JP | 5-65263 A | 3/1993 |
| JP | 7-258194 A | 10/1995 |
| JP | 2002-105035 A | 4/2002 |
| WO | WO 2011/125429 A1 | 10/2011 |

OTHER PUBLICATIONS

PCT International Preliminary Report on Patentability (IPRP) and Written Opinion mailed on Dec. 23, 2015, in corresponding International Application No. PCT/JP2014/071245 (12 pages).
International Search Report (PCT/ISA/210) issued on Nov. 4, 2014, by the Japanese Patent Office as the International Searching Authority for International Application No. PCT/JP2014/071245.
Written Opinion (PCT/ISA/237) issued on Nov. 4, 2014, by the Japanese Patent Office as the International Searching Authority for International Application No. PCT/JP2014/071245.

(Continued)

*Primary Examiner* — Yate K Cutliff
(74) *Attorney, Agent, or Firm* — Buchanan, Ingersoll & Rooney PC

(57) ABSTRACT

A method for producing meta-xylylenediisocyanates includes a reaction step in which monohalogenated benzenes, formaldehydes, and an amide compound represented by general formula (1) below are allowed to react in the presence of an acidic liquid to produce a bisamide compound; a dehalogenation step in which in the bisamide compound, the halogen atom derived from the monohalogenated benzenes is replaced with a hydrogen atom; and a thermal decomposition step in which the bisamide compound from which the halogen atom is eliminated is subjected to thermal decomposition. In the reaction step, the acidic liquid contains inorganic acid, the equivalent ratio of the hydrogen atom of the inorganic acid relative to the monohalogenated benzenes is more than 14, the acidic liquid has an inorganic acid concentration of more than 90 mass %, and the reaction temperature is more than 10° C.

General formula (1):

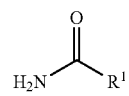

(1)

wherein $R^1$ represents an alkoxy group or an amino group.

6 Claims, No Drawings

(56) References Cited

OTHER PUBLICATIONS

Murai, M. et al., "Gold(I)-Catalyzed Asymmetric Induction of Planar Chirality by Intramolecular Nucleophilic Addition to Chromium-Complexed Alkynylarenes: Asymmetric Synthesis of Planar Chiral (1H-Isochromene and 1,2-Dihydroisoquinoline)Chromium Complexes", The Journal of Organic Chemistry, vol. 78, Scheme 2, Compound 9-10, pp. 10986-10995, Oct. 2, 2013.
Bernacka, E. et al., "Reductive BOC-Amination of Aldehydes", Tetrahedron Letters, vol. 42, Scheme 1, Reference 9, pp. 5093-5094, 2001.
Chernyavskaya et al.: "Synthesis of Aliphatic-Aromatic Diamines Containing Halogen Atoms in Their Benzene Rings", Ukrainskii Khimicheskii Zhurnal, vol. 34, pp. 941-943, 1968 (8 pages including partial English translation).
Liu et al.: "The Synthesis of Sulfonated Phthalimidomethyl Copper Phthalocyanines", Chemical World, the 6th phase, pp. 302-305, 2003 (12 pages including partial English translation).
H. Fan: "Study of Dehalogenation by Hydrogenation of Benzene Halide", Science Press, pp. 377-381, 2001 (6 pages with English Abstract contained in the press).

\* cited by examiner

METHOD FOR PRODUCING META-XYLYLENEDIISOCYANATES

TECHNICAL FIELD

The present invention relates to a method for producing meta-xylylenediisocyanates.

BACKGROUND ART

Metaxylylenediisocyanates are conventionally known for a material of polyurethane used for, for example, paints, adhesives, and plastic lenses. Such metaxylylenediisocyanates are generally produced from metaxylylenediamines, which is produced from metaxylenes.

Patent Document 1 has proposed the following, for example, as a method for producing metaxylylenediamines: metaxylene is subjected to ammoxidation using a fluid catalyst composed of, for example, vanadium to produce isophtalonitrile, and the isophtalonitrile is hydrogenated in the presence of, for example, a nickel catalyst.

CITATION LIST

Patent Document

Patent Document 1: Japanese Unexamined Patent Publication No. 2002-105035

SUMMARY OF THE INVENTION

Problem to be Solved by the Invention

However, when metaxylylenediamine is produced by the method described in Patent Document 1, metaxylene has to be subjected to ammoxidation at a very high temperature of 420° C. to produce isophtalonitrile, and thereafter, the produced isophtalonitrile has to be hydrogenated at a very high pressure of 12 MPa (e.g., Patent Document 1 (Example 1)).

That is, in the method described in Patent Document 1, each of the steps is performed under high temperature and/or high pressure conditions. Therefore, when producing metaxylylenediisocyanate from metaxylylenediamine produced by the method described in Patent Document 1, improvements in facilities and safety are limited.

The present invention is achieved in view of such disadvantages, and its purpose is to provide a method for producing meta-xylylenediisocyanates which does not require high temperature and high pressure (special equipment), and which is excellent in terms of facilities, safety, and economics.

Means for Solving the Problem

A method for producing meta-xylylenediisocyanate of the present invention includes
a reaction step in which monohalogenated benzene, formaldehydes, and an amide compound represented by general formula (1) below are allowed to react in the presence of an acidic liquid to produce a bisamide compound,
a dehalogenation step in which in the bisamide compound, the halogen atom derived from the monohalogenated benzene is replaced with a hydrogen atom, and
a thermal decomposition step in which the bisamide compound from which the halogen atom is eliminated is subjected to thermal decomposition,
wherein in the reaction step,
the acidic liquid contains inorganic acid,
the equivalent ratio of the hydrogen atom of the inorganic acid relative to the monohalogenated benzene is more than 14,
the acidic liquid has an inorganic acid concentration of more than 90 mass %, and
the reaction temperature is more than 10° C.

General formula (1):

[Chem. 1]

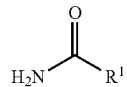

(1)

(in general formula (1), $R^1$ represents an alkoxy group or an amino group).

It is preferable that in the amide compound, $R^1$ in general formula (1) is an n-butoxy group.

It is preferable that in the amide compound, $R^1$ in general formula (1) is a diisobutyl amino group.

It is preferable that the inorganic acid is sulfuric acid or phosphoric acid.

It is preferable that the monohalogenated benzene is monochlorobenzene.

It is preferable that the equivalent ratio of the hydrogen atom of the inorganic acid relative to the monohalogenated benzene is 16 or more, the acidic liquid has an inorganic acid concentration of 95 mass % or more, and the reaction temperature is 20° C. or more.

Effect of the Invention

With the method for producing meta-xylylenediisocyanates of the present invention, monohalogenated benzenes, formaldehydes, and the amide compound represented by the above-described general formula (1) are allowed to react in the presence of an acidic liquid of the above-described conditions at a reaction temperature of more than 10° C. In this manner, for example, a bisamide compound such as a bisurea compound represented by Chemical Formula (2) and Chemical Formula (3) below can be produced.

Chemical Formula (2):

[Chem. 2]

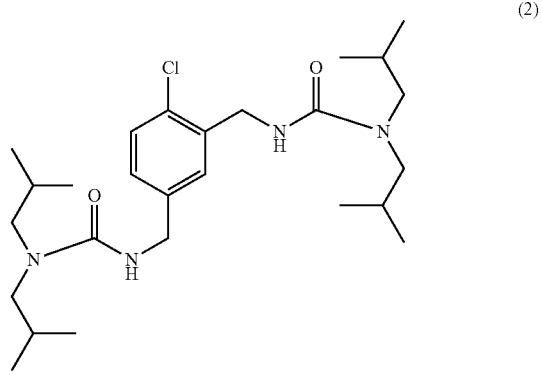

(2)

Chemical Formula (3):

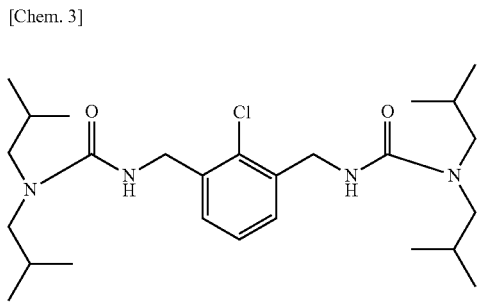

Then, meta-xylylenediisocyanates can be derived from such a bisamide compound by the dehalogenation step and the thermal decomposition step.

Therefore, the method for producing meta-xylylenediisocyanates of the present invention is excellent in terms of facility, safety, and economy, and allows for production of meta-xylylenediisocyanates safely with low costs and high yield. Therefore, the present invention can be suitably used as an industrial production method of meta-xylylenediisocyanates.

DESCRIPTION OF EMBODIMENTS

A method for producing meta-xylylenediisocyanates of the present invention includes a reaction step, a dehalogenation step, and a thermal decomposition step, and preferably, further includes a purification step and a collection step. In the following, each of the steps is described in detail.

[Reaction Step]

In the reaction step, monohalogenated benzenes, formaldehydes, and an amide compound represented by general formula (1) below are allowed to react in the presence of an acidic liquid to produce a bisamide compound.

The monohalogenated benzenes are aromatic compounds in which one of the hydrogen atoms bonded to the benzene ring is replaced with a halogen atom, and examples thereof include monohalogenated benzene represented by general formula (4) below and monohalogenated benzene represented by general formula (5) below.

General formula (4):

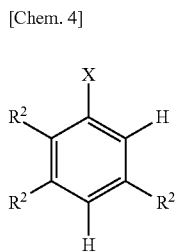

(in general formula (4), X represents a halogen atom. $R^2$ represents a hydrogen atom, an alkyl group, an amino group, a hydroxyl group or an alkoxy group. $R^2$ may be the same or different from each other).

General formula (5):

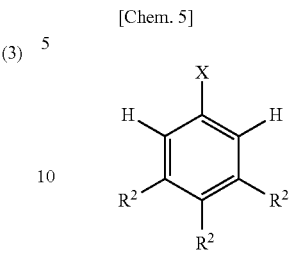

(in general formula (5), X and $R^2$ are the same as X and $R^2$ of the above-described general formula (4)).

In each of general formula (4) and general formula (5), examples of the halogen atom represented by X include a fluorine atom, a chlorine atom, a bromine atom, and an iodine atom. Of these halogen atoms, in view of material costs, preferably, a chlorine atom, a bromine atom, and an iodine atom are used, and even more preferably, a chlorine atom is used.

In each of general formula (4) and general formula (5), examples of the alkyl group represented by $R^2$ include a straight chain alkyl group having 1 to 12 carbon atoms (e.g., methyl group, ethyl group, n-propyl group, n-butyl group, pentyl group, hexyl group, heptyl group, n-octyl group, nonyl group, decyl group, dodecyl group, etc.), a branched alkyl group having 1 to 12 carbon atoms (e.g., isopropyl group, isobutyl group, t-butyl group, isopentyl group, isooctyl group, 2-ethylhexyl group, 2-propylpentyl group, isodecyl group, etc.), and a cycloalkyl group having 3 to 6 carbon atoms (e.g., cyclopropyl group, cyclopentyl group, cyclohexyl group, etc.).

In each of general formula (4) and general formula (5), the amino group represented by $R^2$ can be any of a primary, secondary, and tertiary amino group. Examples of the secondary and tertiary amino groups include an amino group containing, for example, the above-described alkyl group.

In each of general formula (4) and general formula (5), examples of the alkoxy group represented by $R^2$ include an alkoxy group having 1 to 12 carbon atoms (e.g., methoxy group, ethoxy group, propoxy group, butoxy group, etc.).

In each of general formula (4) and general formula (5), of the examples of $R^2$, in view of orientation of monohalogenated benzenes, preferably, a hydrogen atom is used. Furthermore, in each of general formula (4) and general formula (5), all of $R^2$ are preferably the same. In each of general formula (4) and general formula (5), when all of $R^2$ are hydrogen atoms, the monohalogenated benzenes represented by general formula (4) and general formula (5) are the same.

Of these monohalogenated benzenes, in view of material costs and orientation, preferably, monochlorobenzene is used. These examples of monohalogenated benzenes can be used singly, or can be used in combination.

Examples of formaldehydes include formaldehyde and paraformaldehyde, and in view of handleability, preferably, paraformaldehyde is used.

Paraformaldehyde is a homopolymer produced by polymerization of only formaldehyde, and is represented by general formula (6) below.

General Formula (6):

$$HO(CH_2O)nH \qquad (6)$$

(in general formula (6), n represents an integer of 2 or more and 100 or less).

In general formula (6), n represents preferably 8 or more and 100 or less.

Those examples of the formaldehydes can be used singly, or can be used in combination.

Those examples of the formaldehydes are preferably prepared as an aqueous solution in view of handleability. When the formaldehydes are prepared as an aqueous solution, the aqueous solution of formaldehydes has a concentration of, for example, 70 mass % or more, in view of reactivity, preferably 80 mass % or more, for example, 100 mass % or less.

The mixing ratio of the formaldehydes relative to 1 mol of the monohalogenated benzenes is, for example, 1.0 mol or more, in view of the bisamide compound yield, preferably 1.2 mol or more, and for example, 10.0 mol or less, and in view of material costs, preferably 4.0 mol or less.

The mixing ratio of the formaldehydes relative to 100 parts by mass of the monohalogenated benzenes is, for example, 30 parts by mass or more, preferably 40 parts by mass or more, for example, 90 parts by mass or less, preferably 80 parts by mass or less.

The amide compound is represented by general formula (1) below.
General formula (1):

[Chem. 6]

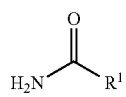

(1)

(in general formula (1), $R^1$ represents an alkoxy group or an amino group).

When $R^1$ is an alkoxy group in general formula (1), the amide compound is carbamate represented by general formula (7) below.
General formula (7):

[Chem. 7]

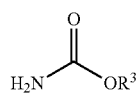

(7)

(in general formula (7), $R^3$ represents an alkyl group).

Examples of the alkyl group represented by $R^3$ in general formula (7) include those given as examples of the alkyl group represented by $R^2$ in general formula (4), and in view of stability of the bisamide compound described later, preferably, a straight chain alkyl group having 1 to 12 carbon atoms, even more preferably, a straight chain alkyl group having 2 to 6 carbon atoms, and particularly preferably, an n-butyl group is used. That is, for $R^1$ in general formula (1) above, preferably, an n-butoxy group is used.

For the carbamate represented by the above-described general formula (7), commercially available products may be used, but those synthesized by a known method can also be used.

To synthesize the carbamate represented by the above-described general formula (7), for example, urea and alcohol are allowed to react.

Examples of the alcohol include a straight chain alcohol having 1 to 12 carbon atoms (e.g., methanol, ethanol, propanol, butanol, pentanol, hexanol, etc.), a branched alcohol having 1 to 12 carbon atoms (e.g., 2-propanol, 2-methylpropylalcohol, t-butylalcohol, 3-methyl-1-butanol, etc.), and cycloalcohol having 3 to 6 carbon atoms (e.g., cyclopentanol, cyclohexanol, etc.). Of these examples of alcohol, preferably, a straight chain alcohol having 1 to 12 carbon atoms is used, and more preferably, butanol (n-butanol) is used. Such examples of alcohol can be used singly, or can be used in combination.

The mixing ratio of alcohol relative to 1 mol of urea is, for example, 0.5 mol or more, in view of the amide compound yield, preferably 0.8 mol or more, and for example, 1.5 mol or less, and in view of material costs, 1.2 mol or less.

The conditions for the reaction between urea and alcohol are as follows: under normal pressure, a temperature of, for example, 80° C. or more, in view of reaction rate, preferably 100° C. or more, and for example, 200° C. or less, in view of safety, preferably 150° C. or less, and a duration of, for example, 1 hour or more, preferably 2 hours or more, for example, 10 hours or less, preferably 6 hours or less.

When $R^1$ in general formula (1) is an amino group, the amide compound is a urea compound represented by general formula (8) below.
General formula (8):

[Chem. 8]

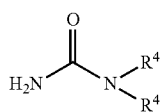

(8)

(in general formula (8), $R^4$ represents a hydrogen atom or an alkyl group. $R^4$ may be the same or different from each other).

Examples of the alkyl group represented by $R^4$ in general formula (8) include those examples given as the alkyl group represented by $R^2$ in general formula (4).

Of those examples of $R^4$ in general formula (8), in view of stability of the bisamide compound described later, preferably, an alkyl group is used, even more preferably, a branched alkyl group having 1 to 12 carbon atoms is used, particularly preferably, a branched alkyl group having 2 to 6 carbon atoms is used, and most preferably, an isobutyl group (2-methylpropyl group) is used. That is, as $R^1$ in the above-described general formula (1), preferably, a diisobutyl amino group is used.

In general formula (8), all of $R^4$ are preferably the same.

For the urea compound represented by the above-described general formula (8), commercially available products may be used, but those synthesized by a known method can also be used.

To synthesize the urea compound represented by the above-described general formula (8), for example, urea and amine are allowed to react.

Examples of the amine include unsubstituted amines, primary amines (e.g., monomethylamine, monoethylamine, mono n-butylamine, mono n-hexylamine, monoisobutylamine, mono t-butylamine, monoisopentylamine, etc.), and secondary amines (e.g., dimethylamine, diethylamine, dibutylamine, dihexylamine, N,N-diisobutylamine, N,N-diisopentylamine, etc.). Of these amines, preferably, secondary amines are used, and more preferably, N,N-diisobutylamine is used. These examples of amines can be used singly, or can be used in combination.

The mixing ratio of amine relative to 1 mol of urea is, for example, 0.5 mol or more, in view of the amide compound yield, preferably 0.8 mol or more, and for example, 1.5 mol or less, and in view of material costs, 1.2 mol or less.

Urea is allowed to react with amine with the following conditions: under normal pressure, a temperature of, for example, 80° C. or more, in view of reaction rate, preferably 100° C. or more, for example, 200° C. or less, and in view of safety, preferably 150° C. or less and a duration of, for example, 1 hour or more, preferably 2 hours or more, and for example, 10 hours or less, preferably 6 hours or less.

The acidic liquid is a liquid containing an inorganic acid, and used also as a reaction solvent in the reaction step. Such an acidic liquid can be composed of only an inorganic acid, or can be an aqueous solution of inorganic acid in which an inorganic acid is dissolved in water.

Examples of the inorganic acid include inorganic acids such as hydrochloric acid, sulfuric acid, nitric acid, phosphoric acid, and boric acid, and in view of the bisamide compound yield, preferably, strong acid, that is, an inorganic acid having an acid dissociation constant (pKa ($H_2O$)) of 3 or less is used. Examples of the strong inorganic acid include, to be specific, hydrochloric acid, sulfuric acid, nitric acid, and phosphoric acid, and in view of the bisamide compound yield, preferably, sulfuric acid and phosphoric acid are used. Such examples of the inorganic acid can be used singly, or can be used in combination.

When the acidic liquid is an aqueous solution of inorganic acid, the acidic liquid have an inorganic acid concentration of, in view of the bisamide compound yield, more than 90 mass %, preferably 95 mass % or more, and for example, less than 100 mass %, and in view of easy preparation of the aqueous solution of inorganic acid, preferably 99 mass % or less.

Those examples of the acidic liquid can be used singly, or can be used in combination. Of these examples of the acidic liquid, preferably, an aqueous solution of sulfuric acid, an aqueous solution of phosphoric acid, and phosphoric acid (substance itself) are used, even more preferably, an aqueous solution of sulfuric acid and phosphoric acid (substance itself) are used.

The mixing ratio of the acidic liquid relative to 100 parts by mass of the monohalogenated benzenes is, for example, 300 parts by mass or more, in view of the bisamide compound yield, preferably 500 parts by mass or more, for example, 3000 parts by mass or less, in view of costs, preferably 2000 parts by mass or less.

The mixing ratio of the inorganic acid relative to 1 mol of the monohalogenated benzenes is, for example, 3 mol or more, in view of the bisamide compound yield, preferably 4 mol or more, more preferably 5 mol or more, for example, 20 mol or less, and in view of costs, preferably 15 mol or less.

The equivalent ratio of the hydrogen atom of the inorganic acid (equivalent ratio in mol) relative to the monohalogenated benzenes is, in view of the bisamide compound yield, more than 14, preferably 16 or more, more preferably 18 or more, for example, 80 or less, in view of costs, preferably 70 or less, even more preferably 60 or less.

To allow the above-described components (monohalogenated benzenes, formaldehydes, and amide compound) to react in the presence of the acidic liquid, first, the components are dissolved or dispersed in the acidic liquid.

To dissolve or disperse the components (monohalogenated benzenes, formaldehydes, and amide compound) in the acidic liquid, for example, the formaldehydes and the amide compound are dissolved in the acidic liquid to prepare an aldehyde-amide solution, and then the aldehyde-amide solution is mixed with the monohalogenated benzenes.

The aldehyde-amide solution can be mixed with the monohalogenated benzenes by a method, without particular limitation, for example, in which one of them is dropped into the other of them, and in view of the bisamide compound yield, preferably, the monohalogenated benzenes are dropped in the aldehyde-amide solution.

The conditions for the dropping are as follows: a temperature of, for example, 0° C. or more, preferably 5° C. or more, for example, 40° C. or less, preferably 30° C. or less, and the dropping time is, for example, 15 minutes or more, preferably 30 minutes or more, for example, 5 hours or less, preferably 3 hours or less.

Then, the mixed solution of the aldehyde-amide solution and the monohalogenated benzenes is heated, thereby allowing the monohalogenated benzenes, formaldehydes, and amide compound to react.

The reaction temperature is, in view of the bisamide compound yield, more than 10° C., preferably 20° C. or more, and more preferably 40° C. or more, particularly preferably 50° C. or more, and in view of facility and safety, for example, 100° C. or less, preferably 90° C. or less, and further preferably 80° C. or less. The reaction temperature within the above-described range is advantageous in that the reaction rate is not reduced and decomposition due to excessive heating does not easily occur.

The reaction pressure is not particularly limited, and can be any of normal pressure, increased pressure, and reduced pressure, and in view of facility and safety, preferably, normal pressure (to be specific, 90 kPa to 110 kPa).

The reaction time is, for example, 1 hour or more, preferably 5 hours or more, for example, 40 hours or less, preferably 30 hours or less, and more preferably less than 20 hours.

In this manner, monohalogenated benzenes, formaldehydes and amide compound are allowed to react in the acidic liquid, thereby highly selectively producing a bisamide compound (disubstituted product).

When a bisamide compound is produced (when two amide compounds are introduced into the aromatic ring), two hydrogen atoms of the monohalogenated benzenes are replaced with the above-described amide compounds. To be more specific, depending on orientation of the monohalogenated benzenes, the hydrogen atoms at positions 2 and 4 of the monohalogenated benzenes are replaced with amide compounds, thereby producing a 2,4-disubstituted product, or hydrogen atoms at positions 2 and 6 of the monohalogenated benzenes are replaced with amide compounds, thereby producing a 2,6-disubstituted product (excellent regioselectivity).

Such 2,4-disubstituted product and 2,6-disubstituted product will both take meta-form when the halogen atoms are replaced with hydrogen atoms in the dehalogenation step described later, regardless of the production ratio.

The production ratio (mol-based) of 2,4-disubstituted product relative to 2,6-disubstituted product is, for example, 3 or more, preferably 5 or more, for example, 15 or less, preferably 20 or less.

The production ratio of 2,4-disubstituted product is calculated from the integrated value of the peak determined by high-performance liquid chromatography (HPLC).

To be more specific, when the monohalogenated benzenes in which all of $R^2$ in the above-described general formula (4) are hydrogen atoms is used as the monohalogenated benzenes, and carbamate represented by the above-described general formula (7) is used as the amide compound, the bisamide compound produced in the reaction step contains a biscarbamate compound (2,4-disubstituted product) represented by general formula (9) below, and a biscarbamate compound (2,6-disubstituted product) represented by general formula (10) below.

General formula (9):

[Chem. 9]

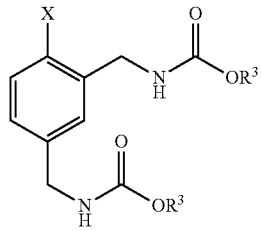

(9)

(in general formula (9), X is the same as X in the above-described general formula (4), $R^3$ is the same as $R^3$ in the above-described general formula (7)).

The biscarbamate compound represented by the above-described general formula (9) is, for example, when all of $R^3$ are butyl groups and X is a chlorine atom, 4-chloro-1,3-xylylenebis(butyl carbamate) (ref: Chemical Formula (16) below).

General formula (10):

[Chem. 10]

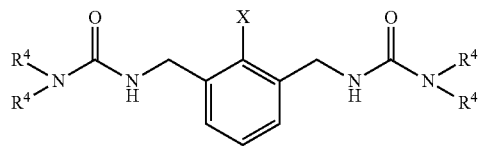

(10)

(in general formula (10), X is the same as X in the above-described general formula (4), $R^3$ is the same as $R^3$ in the above-described general formula (7)).

In the biscarbamate compound represented by the above-described general formula (10), for example, when all of $R^3$ are butyl groups and X is a chlorine atom, 2-chloro-1,3-xylylenebis(butyl carbamate) (ref: Chemical Formula (17) below).

When monohalogenated benzenes in which all of $R^2$ in the above-described general formula (4) are hydrogen atoms is used as the monohalogenated benzenes, and the urea compound represented by the above-described general formula (8) is used as the amide compound, the bisamide compound produced in the reaction step contains a bisurea compound (2,4-disubstituted product) represented by general formula (11) below, and a bisurea compound (2,6-disubstituted product) represented by general formula (12) below.

General formula (11):

[Chem. 11]

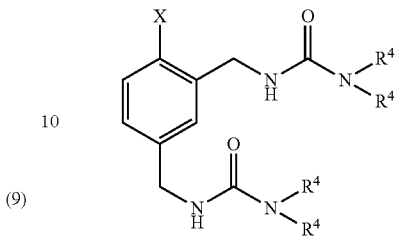

(11)

(in general formula (11), X is the same as X in the above-described general formula (4), and $R^4$ is the same as $R^4$ in the above-described general formula (8)).

The bisurea compound represented by the above-described general formula (11) is, for example, when all of $R^4$ are isobutyl groups and X is a chlorine atom, 4-chloro-1,3-xylylenebis(N,N-diisobutylurea) (ref: Chemical Formula (2)).

General formula (12):

[Chem. 12]

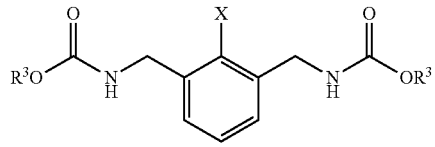

(12)

(in general formula (12), X is the same as X in the above-described general formula (4), $R^4$ is the same as $R^4$ in the above-described general formula (8)).

The bisurea compound represented by the above-described general formula (12) is, for example, when all of $R^4$ are isobutyl groups and X is a chlorine atom, 2-chloro-1,3-xylylenebis(N,N-diisobutylurea)(ref: Chemical Formula (3)).

In the reaction step, the conversion rate of the monohalogenated benzenes is, for example, 80 mol % or more, preferably 85 mol % or more, for example, 100 mol % or less.

The yield of the bisamide compound relative to the monohalogenated benzenes is, for example, 25 mol % or more, preferably 30 mol % or more, more preferably 50 mol % or more, and for example, 100 mol % or less, preferably 80 mol % or less.

The conversion rate of the monohalogenated benzenes and the yield of the bisamide compound are calculated from the integrated value of the peak determined by high-performance liquid chromatography (HPLC).

In the reaction step, in addition to the above-described bisamide compound, a monoamide compound (monosubstituted product) in which one hydrogen atom of the monohalogenated benzenes is replaced with the above-described amide compound may be produced.

In such a case, the yield of the monoamide compound relative to the monohalogenated benzenes is, for example, 1 mol % or more, for example, 40 mol % or less, preferably 35 mol % or less, more preferably 30 mol % or less. The production ratio (mol-based) of the monoamide compound relative to the bisamide compound is, for example, 0.01 or more, and for example, 1.0 or less, preferably 0.9 or less, more preferably 0.6 or less.

The yields of the monoamide compound and the production ratio of the monoamide compound are calculated from the integrated value of the peak determined by high-performance liquid chromatography (HPLC).

The reaction product in the reaction step may contain, in addition to the above-described bisamide compound and the monoamide compound, impurities of the components remained in the reaction (to be specific, formaldehydes, amide compound, inorganic acid, etc.). Therefore, although the reaction product can be used as is, preferably, the reaction product is used after isolation and purification.

The reaction product can be purified by a known purification method, and examples thereof include distillation, solvent extraction, chromatography, crystallization, and recrystallization. In the purification, as necessary, separation and purification by a single purification method can be repeated, or separation and purification by two or more purification methods can be combined. Of these purification methods, in view of convenience, preferably, solvent extraction is used.

To purify the reaction product by solvent extraction, for example, the reaction product is mixed with a mixed solution of water and an organic solvent, and thereafter, the water layer is removed. In this manner, at least the bisamide compound is distributed to the organic solvent (organic layer), and for example, hydrophilic impurities such as formaldehydes and inorganic acids are distributed to the water layer.

The organic solvent is not particularly limited as long as the solvent can dissolve the bisamide compound and cannot dissolve the formaldehydes and amide compound, and examples thereof include weak polar solvents such as saturated hydrocarbons (hexane, heptane, etc.), aromatic hydrocarbons (benzene, toluene, xylene, etc.), and halogenated hydrocarbons (dichloromethane, dichloroethane, carbon tetrachloride, etc.). Of these examples of the organic solvent, in view of affinity with the bisamide compound, preferably, aromatic hydrocarbons are used, even more preferably, toluene is used. These examples of the organic solvent can be used singly, or can be used in combination of two or more.

When the reaction product contains the above-described bisamide compound and monoamide compound, the bisamide compound and the monoamide compound can be separated and purified by, for example, chromatography.

[Dehalogenation Step]

In the dehalogenation step, in the above-described bisamide compound, halogen atom derived from the monohalogenated benzenes is replaced with a hydrogen atom.

The halogen atom of the bisamide compound is replaced with a hydrogen atom by dehalogenation method, for example, a known dehalogenation method from halogenated benzene. Of these examples of the dehalogenation method, preferably, a method in which hydrogen is supplied to the above-described bisamide compound in the presence of a catalyst is used.

Examples of the catalyst include a known hydrogenated catalyst, such as a catalyst containing metals such as Ni, Mo, Fe, Co, Cu, Pt, Pd, and Rh, and in industrial view, preferably, a palladium carbon catalyst is used. Such a catalyst can be used singly, or can be used in combination.

The catalyst is used in an amount of, relative to 100 parts by mass of the monohalogenated benzenes used in the reaction step, for example, 0.5 parts by mass or more, in view of reactivity, preferably 1 part by mass or more, and for example, 7 parts by mass or less, and in view of costs, preferably 8 parts by mass or less.

The catalyst is used in an amount of, relative to 100 parts by mass of the bisamide compound, for example, 0.01 parts by mass or more, in view of reactivity, preferably 0.05 parts by mass or more, and for example, 5 parts by mass or less, in view of costs, preferably 3 parts by mass or less.

To supply hydrogen to the above-described bisamide compound in the presence of the catalyst, for example, a reactor (e.g., autoclave) is charged with the catalyst and the bisamide compound, and thereafter the air in the reactor is replaced with hydrogen.

In these examples of the dehalogenation method, as necessary, a metal salt and an organic solvent are added.

Examples of the metal salt include alkali metal carbonates (e.g., sodium carbonate, potassium carbonate, etc.), alkali metal sulfates (e.g., sodium sulfate, potassium sulfate, etc.), alkaline earth metal carbonates (e.g., magnesium carbonate, calcium carbonate, etc.), and alkaline earth metal sulfates (e.g., magnesium sulfate, calcium sulfate, etc.). Of these examples of the metal salt, preferably, alkali metal carbonates are used, even more preferably, sodium carbonate is used. These examples of the metal salt can be used singly, or can be used in combination.

The mixing ratio of the metal salt relative to 1 mol of the monohalogenated benzenes used in the reaction step is, for example, 0.1 mol or more, in view of trapping the halogen atoms to be eliminated, preferably 0.5 mol or more, for example, 3 mol or less, and in view of costs, preferably 1.5 mol or less.

For the organic solvent, for example, the above-described examples of the organic solvent are used, and preferably, aromatic hydrocarbons, even more preferably, toluene is used. These examples of the organic solvent can be used singly, or can be used in combination of two or more.

When the reaction product is purified by solvent extraction in the reaction step, the organic layer produced in the reaction step can be used as is in the dehalogenation step without adding an organic solvent.

Then, a pressure is applied and the temperature is increased in the reactor, thereby replacing the above-described halogen atom of the bisamide compound with a hydrogen atom.

The reaction conditions in the dehalogenation are as follows: a temperature of, for example, 40° C. or more, in view of reactivity, preferably 70° C. or more, and for example, 150° C. or less, in view of facility and safety, preferably 110° C. or less; and a pressure of, for example, 0.1 MPa or more, in view of reactivity, preferably 0.2 MPa or more, and for example, 3.0 MPa or less, in view of facility and safety, preferably 1.0 MPa or less; and a duration of, for example, 1 hour or more, in view of reactivity, preferably 2 hours or more, for example, 20 hours or less, preferably 10 hours or less.

In this manner, a 1,3-amide-substituted product in which amide compounds are bonded to positions 1 and 3 is produced.

To be more specific, when the monohalogenated benzenes in which all of $R^2$ in the above-described general formula (4) are hydrogen atoms is used as the monohalogenated benzenes, and the carbamate represented by the above-described general formula (7) is used as the amide compound, a 1,3-amide-substituted product represented by general formula (13) below is produced.

General formula (13):

[Chem. 13]

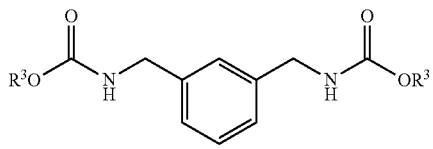
(13)

(in general formula (13), $R^3$ is the same as $R^3$ in the above-described general formula (7)).

That is, both of the biscarbamate compound (2,4-disubstituted product) represented by the above-described general formula (9), and the biscarbamate compound (2,6-disubstituted product) represented by the above-described general formula (10) are converted into the 1,3-amide-substituted product represented by the above-described general formula (13) by the dehalogenation step.

When monohalogenated benzenes in which all of $R^2$ in the above-described general formula (4) are hydrogen atoms is used as the monohalogenated benzenes, and the urea compound represented by the above-described general formula (8) is used as the amide compound, a 1,3-amide-substituted product represented by general formula (14) below is produced.

General formula (14):

[Chem. 14]

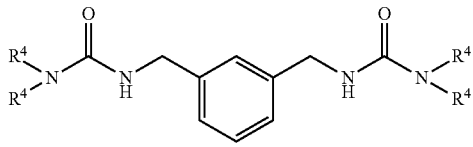
(14)

(in general formula (14), $R^4$ is the same as $R^4$ in the above-described general formula (8)).

That is, both of the biscarbamate compound (2,4-disubstituted product) represented by the above-described general formula (11), and the biscarbamate compound (2,6-disubstituted product) represented by the above-described general formula (12) are converted into the 1,3-amide-substituted product represented by the above-described general formula (14) by the dehalogenation step.

The yield of the 1,3-amide-substituted product relative to the bisamide compound used in the dehalogenation step is, for example, 80 mol % or more, preferably 90 mol % or more, for example, 100 mol % or less, preferably 99 mol % or less.

The yield of the 1,3-amide-substituted product is calculated from the integrated value of the peak determined by high-performance liquid chromatography (HPLC).

[Thermal Decomposition Step]

In the thermal decomposition step, the above-described 1,3-amide-substituted product is subjected to thermal decomposition to produce meta-xylylenediisocyanates.

The thermal decomposition can be performed without particular limitation, and for example, a known decomposition methods such as a liquid phase method and a gas phase method can be performed. In view of workability, preferably, the liquid phase method is used.

To subject the 1,3-amide-substituted product to thermal decomposition by liquid phase method, for example, the 1,3-amide-substituted product and a high boiling point inert solvent are introduced into a reactor equipped with a distillation column, and the 1,3-amide-substituted product is subjected to thermal decomposition.

The reactor is not particularly limited, and for example, a known reactor that is used for a thermal decomposition method can be used. Examples of the distillation column include a packed column and a plate column, and preferably, a packed column is used.

The high boiling point inert solvent is not particularly limited, as long as the high boiling point inert solvent dissolves the 1,3-amide-substituted product, is inert to meta-xylylenediisocyanates, and does not undergo reaction at the time of thermal decomposition (that is, stable), but for performing efficient thermal decomposition reaction, the high boiling point inert solvent has preferably a boiling point higher than the meta-xylylenediisocyanates to be produced.

Examples of the high boiling point inert solvent include aromatic hydrocarbons.

Examples of the aromatic hydrocarbons include benzene (boiling point: 80° C.), toluene (boiling point: 111° C.), o-xylene (boiling point: 144° C.), m-xylene (boiling point: 139° C.), p-xylene (boiling point: 138° C.), ethylbenzene (boiling point: 136° C.), isopropylbenzene (boiling point: 152° C.), butylbenzene (boiling point: 185° C.), cyclohexylbenzene (boiling point: 237 to 340° C.), tetralin (boiling point: 208° C.), chlorobenzene (boiling point: 132° C.), o-dichlorobenzene (boiling point: 180° C.), 1-methylnaphthalene (boiling point: 245° C.), 2-methylnaphthalene (boiling point: 241° C.), 1-chloronaphthalene (boiling point: 263° C.), 2-chloronaphthalene (boiling point: 264 to 266° C.), triphenylmethane (boiling point: 358 to 359° C. (754 mmHg)), 1-phenylnaphthalene (boiling point: 324 to 325° C.), 2-phenylnaphthalene (boiling point: 357 to 358° C.), and biphenyl (boiling point: 255° C.).

Examples of the high boiling point inert solvent also include esters (e.g., dioctyl phthalate, didecyl phthalate, didodecyl phthalate, etc.), and aliphatic hydrocarbons regularly used as a heating medium.

Furthermore, a known process oil and heating medium oil can also be used as the high boiling point inert solvent. Of the known process oil and heating medium oil, preferably, hydrocarbon process oil and hydrocarbon heating medium oil are used. Furthermore, typical known process oil and heating medium oil (commercially available product) include Barrel Process Oil B30 (manufactured by Matsumura Oil Co., Ltd., boiling point: 380° C.), and Barrel Them 400 (manufactured by Matsumura Oil Co., Ltd., boiling point: 390° C.).

Of these examples of the high boiling point inert solvent, in view of yield, preferably, heating medium oil is used. These examples of the high boiling point inert solvent can be used singly, or can be used in combination.

The thermal decomposition temperature can be, for example, 100° C. or more, in view of reaction rate, preferably 150° C. or more, and for example, 400° C. or less, in view of facility and safety, preferably 350° C. or less, more preferably 300° C. or less. The thermal decomposition pressure can be 1000 Pa or more, preferably 5000 Pa or more, and for example, 20000 Pa or less, in view of meta-xylylenediisocyanates separation, preferably 15000 Pa or less. The thermal decomposition time can be, for example, 2 hours or more, preferably 4 hours or more, for example, 40 hours or less, preferably 20 hours or less.

In this manner, the 1,3-amide-substituted product is subjected to thermal decomposition, and meta-xylylenediisocyanates are produced. To be more specific, when the monohalogenated benzenes in which all of $R^2$ in the above-described general formula (4) are hydrogen atoms is used as the monohalogenated benzenes, the meta-xylylenediisocyanate represented by Chemical Formula (15) is produced.
Chemical Formula (15):

[Chem. 15]

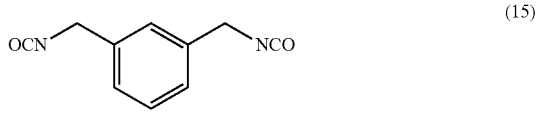

(15)

Then, when meta-xylylenediisocyanates are produced by the above-described liquid phase method, a distillate containing meta-xylylenediisocyanates are produced from the distillation column.

The meta-xylylenediisocyanates yield relative to the 1,3-amide-substituted product used for the thermal decomposition step is, for example, 60 mol % or more, preferably 70 mol % or more, and for example, 100 mol % or less, preferably 99 mol % or less. The meta-xylylenediisocyanates yield is calculated from the integrated value of the peak determined by gas chromatography (GC).

[Purification Step]

The distillate (hereinafter referred to as first distillate) produced in the thermal decomposition step may contain, in addition to meta-xylylenediisocyanates, impurities (e.g., alcohol, amine, etc.) such as by-products of thermal decomposition. Therefore, the first distillate can be used as is, but preferably used after isolation and purification.

Then, in the purification step, the first distillate is purified by the above-described purification method. In the purification method, as necessary, separation and purification by a single purification method can be repeated, and separation and purification by two or more purification methods can be combined. Of these purification methods, in view of industry, preferably, distillation is used.

To purify the first distillate by distillation, for example, the first distillate is introduced into a distillation still equipped with a distillation column, and then the first distillate is subjected to distillation under reduced pressure.

The distillation still is not particularly limited, and for example, a known distillation still is used. For the distillation column, the above-described distillation column can be used, and preferably, plate column is used.

The distillation conditions are as follows: a temperature of, for example, 100° C. or more, preferably 120° C. or more, for example, 300° C. or less, preferably 280° C. or less; a pressure of for example, 10 Pa or more, preferably 50 Pa or more, and for example, 1000 Pa or less, preferably 800 Pa or less; and a duration of, for example, 2 hours or more, preferably 3 hours or more, and for example, 40 hours or less, preferably 20 hours or less.

In this manner, the first distillate is subjected to distillation, and meta-xylylenediisocyanates are produced as distillate (hereinafter referred to as second distillate) from the distillation column.

The purified meta-xylylenediisocyanates have a purity relative to a total amount of the second distillate of, for example, 80 mass % or more, preferably 90 mass % or more, more preferably 95 mass % or more, and for example, 100% or less. The purification yield in the purification step relative to the meta-xylylenediisocyanates used in the purification step is, for example, 70 mol % or more, preferably 80 mol % or more, and for example, 100 mol % or less, preferably 98 mol % or less. The purity of the meta-xylylenediisocyanates and the purification yield in the purification step are calculated from the integrated value of the peak determined by gas chromatography (GC).

[Collection Step]

However, in the thermal decomposition step, alcohol or amine is produced as by-product in the thermal decomposition reaction. Then, these by-products (alcohol and amine) are isolated in the thermal decomposition step and the purification step, for example, by distillation.

Then, in the collection step, the by-product (alcohol or amine) isolated in the thermal decomposition step and in the purification step is allowed to react with urea to produce an amide compound represented by the above-described general formula (1).

The reaction conditions are as follows: a temperature of, for example, 80° C. or more, in view of reactivity, preferably 100° C. or more, and for example, 200° C. or less, in view of safety, preferably 150° C. or less; a pressure of, for example, 90 Pa or more, in view of reactivity, preferably 95 Pa or more, and for example, 110 Pa or less, in view of safety, preferably 100 Pa or less; and a duration of, for example, 1 hour or more, preferably 2 hours or more, and for example, 40 hours or less, preferably 20 hours or less.

In this manner, the amide compound represented by the above-described general formula (1), that is, the amide compound used in the reaction step is produced. Therefore, the amide compound collected in the collection step can be used in the reaction step, which allows for further improvement in economy.

The method for producing meta-xylylenediisocyanates allows for production of meta-xylylenediisocyanates safely at low costs with a high yield by simple processes and under mild conditions relative to conventional methods. Therefore, the method for producing meta-xylylenediisocyanates is excellent in terms of facility, safety, and economy. As a result, the method for producing meta-xylylenediisocyanates can be suitably used as an industrial production.

The meta-xylylenediisocyanates and its salt are suitably used as various industrial materials including resin material of, for example, polyurethane material. Particularly, they are suitable for applications in polyurethane paints, adhesives, sealants, and elastomers, and polythiourethane-based lenses.

Meta-xylylenediisocyanate produced by the method for producing meta-xylylenediisocyanates of the present invention does not substantially contain acid component and a hydrolysable chlorine (HC) component, unlike those derived by the method (phosgene method) using phosgene from meta-xylylenediamines. To be specific, meta-xylylenediisocyanates have a hydrolysable chlorine (HC) concentration of, for example, 5000 ppm or less, preferably 1000 ppm or less. The hydrolysable chlorine (HC) concentration is measured in conformity with the determination of hydrolysable chlorine described in JIS K 1603-3 (2007).

The hydrolysable chlorine (HC) concentration of the above-described upper limit or less allows for a reduced amount of impurities in meta-xylylenediisocyanates, and suppression of coloring over time of meta-xylylenediisocyanates.

[Stabilizing Agent]

However, the hydrolysable chlorine (HC) concentration of the above-described upper limit or less may cause cloudiness due to, for example, self-polymerization of meta-xylylenediisocyanates.

Therefore, as necessary, an acid component (hydrochloric acid, etc.), and a known, public use stabilizing agent is preferably added to meta-xylylenediisocyanates.

To the meta-xylylenediisocyanates, depending on its purpose and applications, known additives such as a urethanizing catalyst, an organic catalyst, a filler, an ultraviolet absorber, and an antioxidant can be suitably added.

EXAMPLES

In the following, the present invention will be described in detail with reference to Examples. However, the present invention is not limited thereto. The formulations, acidic liquids, reaction conditions, conversion rate, and yields in the reaction step for Examples and Comparative Examples are shown in Table 1.

Values such as mixing ratios in Examples can be replaced with the upper limit values or lower limit values in corresponding values in the above-described embodiments.

Furthermore, the components in each of the steps are analyzed with gas chromatography (GC) or high-performance liquid chromatography (HPLC). To be more specific, a three-point calibration curve is prepared, and based on the integrated value of the peak produced by GC or HPLC, the concentration and content of each component were calculated.

Example 1

Reaction Step

A 1 L flask equipped with a stirrer, a thermometer, and a gas discharge pipe was charged with 120.2 g (2.0 mol) of urea and 148.2 g (2.0 mol) of n-butanol, and thereafter they were heated to about 130° C. The mixture was stirred for 4 hours while the temperature was kept constant. Thereafter, the mixture was cooled to 25° C., thereby producing a crude product. The crude product was analyzed by GC, and it was found that the crude product contained n-butyl carbamate, and the n-butyl carbamate yield was 96.9 mol % relative to urea. In this manner, the crude product containing 227.2 g of n-butyl carbamate was produced.

Then, a 1 L four-neck flask equipped with a stirrer, a dropping funnel, a thermometer, and a gas discharge pipe was charged with 515.8 g (sulfuric acid: 5.0 mol) of 95 mass % aqueous solution of sulfuric acid, and 117.2 g (1.0 mol) of n-butyl carbamate, and 33.4 g (formaldehyde: 1.0 mol) of 90 mass % aqueous solution of paraformaldehyde, and they were dissolved in 95 mass % aqueous solution of sulfuric acid, thereby preparing an aldehyde-carbamic acid solution (aldehyde-amide solution).

Then, while the temperature in the flask was kept in the temperature range of 10 to 20° C., 56.3 g (0.5 mol) of monochlorobenzene was dropped to the aldehyde-carbamic acid solution taking 1 hour (dropping speed: $8.3 \times 10^{-3}$ mol/min). That is, the equivalent ratio (molar ratio) of the hydrogen atom of sulfuric acid relative to the monohalogenated benzenes was 20.

Thereafter, the temperature in the flask was increased to 60° C. (reaction temperature), and while the temperature was kept constant, the components were allowed to react under normal pressure. After 8 hours (reaction time), the reaction was terminated, and a reaction product was obtained.

The reaction product was analyzed with HPLC, and it was found that the monochlorobenzene conversion rate was 92%, and the reaction product contained biscarbamate compound (disubstituted product), and the monocarbamate compound (monosubstituted product).

Relative to monochlorobenzene, the biscarbamate compound (disubstituted product) yield was 71%, and the monocarbamate compound (monosubstituted product) yield was 2%. That is, biscarbamate compound was produced in a total of 0.36 mol, and its total mass was 131.5 g.

The produced biscarbamate compound contained only a biscarbamate compound (2,4-disubstituted product) represented by Chemical Formula (16) below and a biscarbamate compound (2,6-disubstituted product) represented by Chemical Formula (17) below.

Chemical Formula (16):

[Chem. 16]

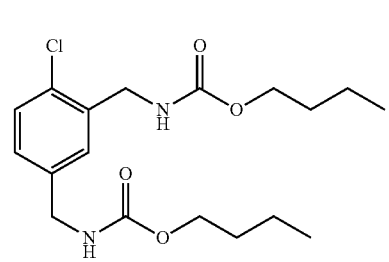

(16)

Chemical Formula (17):

[Chem. 17]

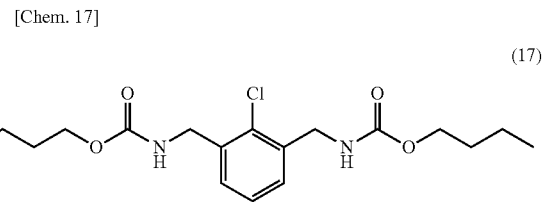

(17)

The isomer ratio of 2,4-disubstituted product to 2,6-disubstituted product was 10 (2,4-disubstituted product):1 (2,6-disubstituted product).

The monochlorobenzene conversion rate, the biscarbamate compound yield, the monocarbamate compound yield, and the isomer ratio of 2,4-disubstituted product to 2,6-disubstituted product were calculated from the integrated value of the peak determined by high-performance liquid chromatography (HPLC).

A 2 L flask having a drain cock and equipped with stirrer was charged with 500 g of toluene and 500 g of water, then the above-described total amount of the reaction products was dropped taking 15 minutes, and the mixture was stirred.

Then, after taking out the water layer, 500 g of water was added again to the organic layer, and the mixture was stirred. This was repeated four times to wash the organic layer with water, thereby producing an organic layer (bisamide solution) in which the biscarbamate compound and the monocarbamate compound were dissolved. That is, the organic layer had a biscarbamate compound concentration of 20.8 mass %.

[Dehalogenation Step]

Then, a 1 L autoclave equipped with a stirrer was charged with 1.5 g of palladium carbon (catalyst) and 53.0 g (0.5 mol) of sodium carbonate anhydride, and then the total amount of the above-described organic layer was introduced thereto.

Then, the gas phase portion in the autoclave was replaced with nitrogen, then replaced with hydrogen, and the hydrogen pressure was increased to 0.5 MPa. Furthermore, the temperature in the autoclave was increased to 90° C. to advance the dehalogenation reaction of the biscarbamate compound. The reaction was terminated after 5 hours and cooling was performed.

The reaction solution after the cooling was filtered to separate the catalyst and the inorganic salt (sodium chloride), thereby producing a filtrate. Then, the solvent (toluene) was distilled off from the filtrate, thereby producing N,N'-meta-xylylenebis(butyl carbamate) as 1,3-carbamate substituted product. The N,N'-meta-xylylenebis(butyl carbamate) yield relative to the total of the biscarbamate compound represented by Chemical Formula (2) and Chemical Formula (3) was 97 mol %. That is, 0.34 mol of N,N'-meta-xylylenebis(butyl carbamate) was produced, and its mass was 115.8 g.

The N,N'-meta-xylylenebis(butyl carbamate) yield was calculated from the integrated value of the peak determined by high-performance liquid chromatography (HPLC).

[Thermal Decomposition Step]

A reactor equipped with a packed column was charged with a high boiling point inert solvent (trade name: Barrel Therm 400, manufactured by Matsumura Oil Co., Ltd.), and a total amount of N,N'-meta-xylylenebis(butyl carbamate) produced in the dehalogenation step. Then, the pressure in the reactor was reduced to 100 torr (13.3 KPa) or less, and heating was performed to give a temperature in the range of 200° C. to 300° C., thereby performing thermal decomposition of N,N'-meta-xylylenebis(butyl carbamate).

Then, the distillate (first distillate) from the packed column was collected. The distillate was analyzed by GC, and production of meta-xylylenediisocyanate was confirmed. The meta-xylylenediisocyanate yield relative to the N,N'-meta-xylylenebis(butyl carbamate) was 80 mol %. That is, 0.28 mol of meta-xylylenediisocyanate was produced, and its mass was 51.9 g.

[Purification Step]

A distillation still equipped with a plate column having distillation plates equivalent to ten and a capillary tube connected to a nitrogen line was charged with the distillate produced in the thermal decomposition step. Then, distillation under reduced pressure was performed under a pressure range of 0.5 to 5 torr (66.7 Pa to 666.7 Pa), and a temperature range of 160° C. to 240° C. Then, the distillate (second distillate) from the plate column was collected, thereby producing purified meta-xylylenediisocyanate. The purified meta-xylylenediisocyanate was analyzed by GC, and it was found that the meta-xylylenediisocyanate had a purity of 99.7 mass %, and a purification yield relative to the meta-xylylenediisocyanate used in the purification step was 93 mol %. That is, 0.26 mol of meta-xylylenediisocyanate was collected, and its mass was 48.3 g.

Example 2

Meta-xylylenediisocyanate was prepared in the same manner as in Example 1, except that in the reaction step, the amount of the 95 mass % aqueous solution of sulfuric acid used was changed to 464.6 g (sulfuric acid: 4.5 mol).

In the reaction step, the monochlorobenzene conversion rate was 92 mol %, the biscarbamate compound (disubstituted product) yield was 66 mol %, and the monocarbamate compound (monosubstituted product) yield was 6 mol %.

Example 3

Meta-xylylenediisocyanate was prepared in the same manner as in Example 1, except that in the reaction step, the amount of the 95 mass % aqueous solution of sulfuric acid used was changed to 413.0 g (sulfuric acid: 4.0 mol).

In the reaction step, the monochlorobenzene conversion rate was 91 mol %, the biscarbamate compound (disubstituted product) yield was 39 mol %, and the monocarbamate compound (monosubstituted product) yield was 35 mol %.

Example 4

Meta-xylylenediisocyanate was prepared in the same manner as in Example 1, except that in the reaction step, 515.8 g (sulfuric acid: 5.0 mol) of 95 mass % aqueous solution of sulfuric acid was changed to 500.4 g (sulfuric acid: 5.0 mol) of 98 mass % aqueous solution of sulfuric acid, and the reaction temperature was changed to 70° C.

In the reaction step, the monochlorobenzene conversion rate was 93 mol %, the biscarbamate compound (disubstituted product) yield was 63 mol %, and the monocarbamate compound (monosubstituted product) yield was 2 mol %.

Example 5

Meta-xylylenediisocyanate was prepared in the same manner as in Example 1, except that in the reaction step, the amount of the 90 mass % aqueous solution of paraformaldehyde used was changed to 41.8 g (formaldehyde: 1.25 mol), and 515.8 g (sulfuric acid: 5.0 mol) of 95 mass % aqueous solution of sulfuric acid was changed to 500.4 g (sulfuric acid: 5.0 mol) of 98 mass % aqueous solution of sulfuric acid.

In the reaction step, the monochlorobenzene conversion rate was 92 mol %, the biscarbamate compound (disubstituted product) yield was 65 mol %, and the monocarbamate compound (monosubstituted product) yield was 6 mol %.

Example 6

Meta-xylylenediisocyanate was prepared in the same manner as in Example 1, except that in the reaction step, the amount of the 90 mass % aqueous solution of paraformaldehyde used was changed to 41.8 g (formaldehyde: 1.25 mol), and 515.8 g (sulfuric acid: 5.0 mol) of 95 mass % aqueous solution of sulfuric acid was changed to 1000.0 g (phosphoric acid: 10 mol) of 98 mass % aqueous solution of phosphoric acid.

In the reaction step, the monochlorobenzene conversion rate was 90 mol %, the biscarbamate compound (disubstituted product) yield was 51 mol %, and the monocarbamate compound (monosubstituted product) yield was 27 mol %.

Example 7

Meta-xylylenediisocyanate was prepared in the same manner as in Example 1, except that in the reaction step, the amount of 90 mass % aqueous solution of paraformaldehyde was changed to 41.8 g (formaldehyde: 1.25 mol), and 515.8 g (sulfuric acid: 5.0 mol) of 95 mass % aqueous solution of sulfuric acid was changed to 980.0 g (phosphoric acid: 10 mol) of phosphoric acid.

In the reaction step, the monochlorobenzene conversion rate was 92 mol %, the biscarbamate compound (disubstituted product) yield was 72 mol %, and the monocarbamate compound (monosubstituted product) yield was 5 mol %.

Example 8

Meta-xylylenediisocyanate was prepared in the same manner as in Example 1, except that in the reaction step, the amount of 90 mass % aqueous solution of paraformaldehyde used was changed to 41.8 g (formaldehyde: 1.25 mol), 515.8 g (sulfuric acid: 5.0 mol) of 95 mass % aqueous solution of sulfuric acid was changed to 500.4 g (sulfuric acid: 5.0 mol) of 98 mass % aqueous solution of sulfuric acid, the reaction temperature was changed to 20° C., and the reaction time was changed to 20 hours.

In the reaction step, the monochlorobenzene conversion rate was 92 mol %, the biscarbamate compound (disubstituted product) yield was 44 mol %, and the monocarbamate compound (monosubstituted product) yield was 32 mol %.

Example 9

A 1 L flask equipped with a stirrer, a thermometer, and a gas discharge pipe was charged with 120.2 g (2.0 mol) of urea, and 258.4 g (2.0 mol) of N,N-diisobutylamine, and then thereafter they were heated to about 130° C. The mixture was stirred for 4 hours while the temperature was kept constant. Thereafter, the mixture was cooled to 25° C., thereby producing a crude product. The crude product was analyzed by GC, and it was found that the crude product contained N,N-diisobutylurea, and the N,N-diisobutylurea yield was 98 mol % relative to urea. In this manner, the crude product containing 337.8 g of N,N-diisobutylurea was produced.

Then, a 1 L four-neck flask equipped with a stirrer, a dropping funnel, a thermometer, and a gas discharge pipe was charged with 515.8 g (sulfuric acid: 5.0 mol) of 95 mass % aqueous solution of sulfuric acid, and further charged with 172.3 g (1.0 mol) of N,N-diisobutylurea, and 33.4 g (formaldehyde: 1.0 mol) of 90 mass % aqueous solution of paraformaldehyde, and they were dissolved in 95 mass % aqueous solution of sulfuric acid, thereby preparing an aldehyde-urea solution (aldehyde-amide solution).

Then, while the temperature of the flask was kept in the temperature range of 10 to 20° C., 56.3 g (0.5 mol) of monochlorobenzene was dropped to the aldehyde-urea solution taking 1 hour (dropping speed: $8.3 \times 10^{-3}$ mol/min). That is, the equivalent ratio (molar ratio) of the hydrogen atom of sulfuric acid relative to the monohalogenated benzenes was 20.

Thereafter, the temperature in the flask was increased to 50° C. (reaction temperature), and while the temperature was kept constant, the components were allowed to react under normal pressure. After 5 hours (reaction time), the reaction was terminated, and a reaction product was obtained.

The reaction product was analyzed with HPLC, and it was found that the monochlorobenzene conversion rate was 95 mol %, and the reaction product contained the bisurea compound (disubstituted product) and the monourea compound (monosubstituted product).

Relative to monochlorobenzene, the bisurea compound (disubstituted product) yield was 62 mol %, and the monourea compound (monosubstituted product) yield was 5 mol %. That is, the bisurea compound was produced in a total of 0.31 mol, and its total mass was 149.1 g.

The results of mass spectroscopy on the bisurea compound (disubstituted product) showed [M+]=m/z 481 ([measurement conditions], ionization method: FAB (pos), matrix: m-NBA).

The produced bisurea compound contained only the bisurea compound (2,4-disubstituted product) represented by Chemical Formula (2) below and the bisurea compound (2,6-disubstituted product) represented by Chemical Formula (3) below.

Chemical Formula (2):

[Chem. 18]

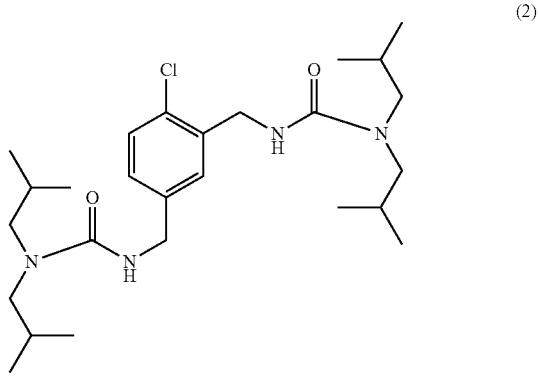

(2)

Chemical Formula (3):

[Chem. 19]

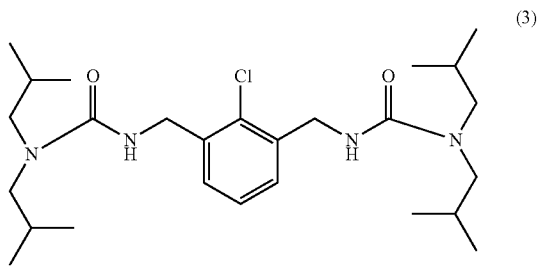

(3)

A 2 L flask having a drain cock and equipped with a stirrer was charged with 500 g of toluene and 500 g of water, and thereafter, a total amount of the reaction products was introduced therein by dropping for 15 minutes, and the mixture was stirred.

Then, after taking out the water layer, 500 g of water was added again to the organic layer, and the mixture was stirred. This was repeated four times to wash the organic layer with water, thereby producing an organic layer (bisurea compound solution) in which the bisurea compound and the monourea compound were dissolved. That is, the organic layer had a bisurea compound concentration of 20.9 mass %.

[Dehalogenation Step]

Then, a 1 L autoclave equipped with a stirrer was charged with 1.5 g of palladium carbon (catalyst) and 53.0 g (0.5 mol) of sodium carbonate anhydride, and thereafter a total amount of the above-described organic layer was further introduced thereto.

Then, the gas phase portion in the autoclave was replaced with nitrogen, then replaced with hydrogen, and the hydrogen pressure was increased to 0.5 MPa. Furthermore, the temperature in the autoclave was increased to 90° C. to advance the dehalogenation reaction of the bisurea compound. The reaction was terminated after 5 hours and cooling was performed.

The reaction solution after the cooling was filtered to separate the catalyst and the inorganic salt (sodium chloride), thereby producing a filtrate. Then, the solvent (toluene) was distilled off from the filtrate, thereby producing N,N'-meta-xylylenebis(N,N-diisobutylurea) as the 1,3-urea substituted product.

The results of mass spectroscopy on N,N'-meta-xylylenebis(N,N-diisobutylurea) showed $[M+H]^+=m/z$ 447 ([measurement conditions], ionization method: FAB (pos), matrix: m-NBA).

The N,N'-meta-xylylenebis(N,N-diisobutylurea) yield relative to a total of the bisurea compounds represented by the above-described Chemical Formula (2) and represented by Chemical Formula (3) was 95 mol %. That is, 0.29 mol of N,N'-meta-xylylenebis(N,N-diisobutylurea) was produced, and its mass was 129.5 g.

The N,N'-meta-xylylenebis(N,N-diisobutylurea) yield was calculated from the integrated value of the peak determined by high-performance liquid chromatography (HPLC).

[Thermal Decomposition Step]

A reactor equipped with a packed column was charged with a high boiling point inert solvent (trade name: Barrel Process Oil B30, manufactured by Matsumura Oil Co., Ltd.), and a total amount of N,N'-meta-xylylenebis(N,N-diisobutylurea) produced in the dehalogenation step. Then, the pressure in the reactor was reduced to 100 torr (13.3 KPa) or less, and heating was performed to a temperature range of 200° C. to 300° C., thereby subjecting N,N'-meta-xylylenebis(N,N-diisobutylurea) to thermal decomposition.

Then, the distillate (first distillate) from the packed column was collected. The distillate was analyzed with GC, and production of meta-xylylenediisocyanate was confirmed. The meta-xylylenediisocyanate yield relative to N,N'-meta-xylylenebis(N,N-diisobutylurea) was 68 mol %. That is, 0.20 mol of meta-xylylenediisocyanate was produced, and its mass was 37.6 g.

[Purification Step]

A distillation still equipped with a plate column having distillation plates equivalent to ten and a capillary tube connected to a nitrogen line was charged with the distillate produced in the thermal decomposition step. Then, distillation under reduced pressure was performed under a pressure range of 0.5 to 5 torr (66.7 Pa to 666.7 Pa), and a temperature range of 160° C. to 240° C. The distillate (second distillate) from the plate column was collected, thereby producing purified meta-xylylenediisocyanate. The purified meta-xylylenediisocyanate was analyzed by GC, and it was found that the meta-xylylenediisocyanate had a purity of 99.8 mass %, and a purification yield relative to the meta-xylylenediisocyanate used in the purification step was 90 mol %. That is, 0.18 mol of meta-xylylenediisocyanate was collected, and its mass was 33.9 g.

Comparative Example 1

The steps were performed in the same manner as in Example 1, except that in the reaction step, the amount of the aqueous solution of sulfuric acid used was changed to 361.3 g (sulfuric acid: 3.5 mol).

In the reaction step, the monochlorobenzene conversion rate was 30 mol %, and the monocarbamate compound (monosubstituted product) yield was 6 mol %. The biscarbamate compound (disubstituted product) was not produced.

Comparative Example 2

The steps were performed in the same manner as in Example 1, except that in the reaction step, 515.8 g (sulfuric acid: 5.0 mol) of 95 mass % aqueous solution of sulfuric acid was changed to 544.9 g (sulfuric acid: 5.0 mol) of 90 mass % aqueous solution of sulfuric acid.

In the reaction step, the monochlorobenzene conversion rate was 45 mol %, the biscarbamate compound (disubstituted product) yield was 9 mol %, and the monocarbamate compound (monosubstituted product) yield was 9 mol %.

Comparative Example 3

The steps were performed in the same manner as in Example 1, except that in the reaction step, the amount of 90 mass % aqueous solution of paraformaldehyde used was changed to 41.8 g (formaldehyde: 1.25 mol), and 515.8 g (sulfuric acid: 5.0 mol) of 95 mass % aqueous solution of sulfuric acid was changed to 1088.9 g (phosphoric acid: 10 mol) of the 90 mass % aqueous solution of phosphoric acid.

In the reaction step, the monochlorobenzene conversion rate was 27 mol %, and the monocarbamate compound (monosubstituted product) yield was 5 mol %. The biscarbamate compound (disubstituted product) was not produced.

Comparative Example 4

The steps were performed in the same manner as in Example 1, except that in the reaction step, the amount of 90 mass % aqueous solution of paraformaldehyde used was changed to 41.8 g (formaldehyde: 1.25 mol), 515.8 g (sulfuric acid: 5.0 mol) of 95 mass % aqueous solution of sulfuric acid was changed to 500.4 g (sulfuric acid: 5.0 mol) of 98 mass % aqueous solution of sulfuric acid, the reaction temperature was changed to 10° C., and the reaction time was changed to 20 hours.

In the reaction step, the monochlorobenzene conversion rate was 87 mol %, the biscarbamate compound (disubstituted product) yield was 2 mol %, and the monocarbamate compound (monosubstituted product) yield was 70 mol %.

Comparative Example 5

The steps were performed in the same manner as in Example 1, except that in the reaction step, 515.8 g (sulfuric acid: 5.0 mol) of 95 mass % aqueous solution of sulfuric acid was changed to 970.7 g (methanesulfonic acid: 10.0 mol) of 99 mass % aqueous solution of methanesulfonic acid, and the reaction temperature was changed to 80° C.

In the reaction step, the monochlorobenzene conversion rate was 2 mol %, and the biscarbamate compound (disubstituted product) and the monocarbamate compound (monosubstituted product) were not produced.

Comparative Example 6

The steps were performed in the same manner as in Example 1, except that in the reaction step, 515.8 g (sulfuric acid: 5.0 mol) of 95 mass % aqueous solution of sulfuric acid was changed to 606.6 g (acetic acid: 10.0 mol) of 99 mass % aqueous solution of acetic acid, and the reaction temperature was changed to 100° C.

In the reaction step, the monochlorobenzene conversion rate was 0%, and the biscarbamate compound (disubstituted product) and the monocarbamate compound (monosubstituted product) were not produced.

Comparative Example 7

The steps were performed in the same manner as in Example 1, except that in the reaction step, 56.3 g (0.5 mol) of chlorobenzene was changed to 39.1 g (0.5 mol) of benzene.

In the reaction step, the monochlorobenzene conversion rate was 100 mol %, the biscarbamate compound (disubstituted product) yield was 18 mol %, and the monocarbamate compound (monosubstituted product) yield was 1 mol %. Analysis with HPLC revealed that the biscarbamate compound (disubstituted product) contained 54 mol % of 1,2-carbamate substituted product and 1,4-carbamate substituted product relative to the total amount of the biscarbamate compound.

Comparative Example 8

The steps were performed in the same manner as in Example 9, except that in the reaction step, the amount of the aqueous solution of sulfuric acid used was changed to 361.3 g (sulfuric acid: 3.5 mol).

In the reaction step, the monochlorobenzene conversion rate was 26 mol %, and the monourea compound (monosubstituted product) yield was 5%. The bisurea compound (disubstituted product) was not produced.

BIBU: N,N-diisobutylurea
MSA: methanesulfonic acid (Manufactured by Wako Pure Chemical Industries, Ltd.)

While the illustrative embodiments of the present invention are provided in the above description, such is for illustrative purpose only and it is not to be construed as limiting in any manner Modification and variation of the present invention that will be obvious to those skilled in the art is to be covered by the following claims.

INDUSTRIAL APPLICABILITY

With the present invention, meta-xylylenediisocyanates can be produced under comparatively mild conditions relative to conventional methods. Therefore, in view of facilities, safety, and economy, meta-xylylenediisocyanates can be produced more industrially and advantageously.

The meta-xylylenediisocyanates are used suitably for applications in polyurethane and polythiourethane for higher performance. Particularly, it is suitable for applications in polyurethane paints, adhesives, sealants, elastomers, and polythiourethane-based lenses.

The invention claimed is:
1. A method for producing meta-xylylenediisocyanate, comprising:
 reacting monohalogenated benzene, formaldehydes, and an amide compound represented by formula (1) below in the presence of an acidic liquid to produce a bisamide compound,
 dehalogenating the bisamide compound wherein a halogen atom derived from the monohalogenated benzene is replaced with a hydrogen atom, and
 thermally decomposing the bisamide compound from which the halogen atom is eliminated,
 wherein in the reacting of the monohalogenated benzene, formaldehydes, and the amide compound,
 the acidic liquid contains inorganic acid,
 an equivalent ratio of the hydrogen atom of the inorganic acid relative to the monohalogenated benzene is more than 14,

TABLE 1

| | Formulation (molar ratio) | | | | | Acidic Liquid | | Reaction Conditions | | Conversion Rate (%) | Disubstituted Product Yield (%) | Monosubstituted Product Yield (%) |
|---|---|---|---|---|---|---|---|---|---|---|---|---|
| No. | CB | BZ | PFA | BC | BIBU | Acid Type | Concentration (mass %) | Acid equivalent (H/CB) | Temperature | Time | | | |
| Ex. 1 | 1.0 | — | 2.0 | 2.0 | — | Sulfuric acid | 95 | 20 | 60 | 8 | 92 | 71 | 2 |
| Ex. 2 | 1.0 | — | 2.0 | 2.0 | — | Sulfuric acid | 95 | 18 | 60 | 8 | 92 | 66 | 6 |
| Ex. 3 | 1.0 | — | 2.0 | 2.0 | — | Sulfuric acid | 95 | 16 | 60 | 8 | 91 | 39 | 35 |
| Ex. 4 | 1.0 | — | 2.0 | 2.0 | — | Sulfuric acid | 98 | 20 | 70 | 8 | 93 | 63 | 2 |
| Ex. 5 | 1.0 | — | 2.5 | 2.0 | — | Sulfuric acid | 98 | 20 | 60 | 8 | 92 | 65 | 6 |
| Ex. 6 | 1.0 | — | 2.5 | 2.0 | — | Phosphoric acid | 98 | 60 | 60 | 8 | 90 | 51 | 27 |
| Ex. 7 | 1.0 | — | 2.5 | 2.0 | — | Phosphoric acid | 100 | 60 | 60 | 8 | 92 | 72 | 5 |
| Ex. 8 | 1.0 | — | 2.5 | 2.0 | — | Sulfuric acid | 98 | 20 | 20 | 20 | 92 | 44 | 32 |
| Ex. 9 | 1.0 | — | 2.0 | — | 2.0 | Sulfuric acid | 95 | 20 | 50 | 5 | 95 | 62 | 5 |
| Comp. Ex. 1 | 1.0 | — | 2.0 | 2.0 | — | Sulfuric acid | 95 | 14 | 60 | 8 | 30 | 0 | 6 |
| Comp. Ex. 2 | 1.0 | — | 2.0 | 2.0 | — | Sulfuric acid | 90 | 20 | 60 | 8 | 45 | 9 | 9 |
| Comp. Ex. 3 | 1.0 | — | 2.5 | 2.0 | — | Phosphoric acid | 90 | 60 | 60 | 8 | 27 | 0 | 5 |
| Comp. Ex. 4 | 1.0 | — | 2.5 | 2.0 | — | Sulfuric acid | 98 | 20 | 10 | 20 | 87 | 2 | 70 |
| Comp. Ex. 5 | 1.0 | — | 2.0 | 2.0 | — | MSA | 99 | 20 | 80 | 8 | 2 | 0 | 0 |
| Comp. Ex. 6 | 1.0 | — | 2.0 | 2.0 | — | Acetic Acid | 99 | 20 | 100 | 8 | 0 | 0 | 0 |
| Comp. Ex. 7 | — | 1.0 | 2.0 | 2.0 | — | Sulfuric acid | 95 | 20 | 60 | 8 | 100 | 18 | 1 |
| Comp. Ex. 8 | 1.0 | — | 2.0 | — | 2.0 | Sulfuric acid | 95 | 14 | 60 | 8 | 26 | 0 | 5 |

The abbreviations in Table 1 are shown below.
CB: monochlorobenzene (manufactured by Tokyo Chemical Industry Co., Ltd.)
BZ: benzene (manufactured by Wako Pure Chemical Industries, Ltd.)
PFA: paraformaldehyde (manufactured by Tokyo Chemical Industry Co., Ltd.)
BC: n-butyl carbamate (manufactured by Tokyo Chemical Industry Co., Ltd.)

the acidic liquid has an inorganic acid concentration of more than 90 mass %, and a reaction temperature is more than 10° C.:

formula (1):

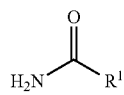

wherein $R^1$ represents an alkoxy group or an amino group.

2. The method for producing meta-xylylenediisocyanate according to claim 1, wherein $R^1$ in formula (1) is an n-butoxy group.

3. The method for producing meta-xylylenediisocyanate according to claim 1, wherein $R^1$ in formula (1) is a diisobutyl amino group.

4. The method for producing meta-xylylenediisocyanate according to claim 1, wherein the inorganic acid is sulfuric acid or phosphoric acid.

5. The method for producing meta-xylylenediisocyanate according to claim 1, wherein the monohalogenated benzene is monochlorobenzene.

6. The method for producing meta-xylylenediisocyanate according to claim 1, wherein the equivalent ratio of the hydrogen atom of the inorganic acid relative to the monohalogenated benzene is 16 or more, the acidic liquid has an inorganic acid concentration of 95 mass % or more, and the reaction temperature is 20° C. or more.

* * * * *